US012759962B2

(12) United States Patent
Lyu et al.

(10) Patent No.: US 12,759,962 B2
(45) Date of Patent: Oct. 13, 2026

(54) METHOD FOR PREPARING ACRYLIC ACID

(71) Applicant: LG CHEM, LTD., Seoul (KR)

(72) Inventors: Byeong Gil Lyu, Daejeon (KR); Mi Kyung Kim, Daejeon (KR); Dae Young Shin, Daejeon (KR); Da Bin Jung, Daejeon (KR)

(73) Assignee: LG CHEM, LTD., Seoul (KR)

(*) Notice: Subject to any disclaimer, the term of this patent is extended or adjusted under 35 U.S.C. 154(b) by 471 days.

(21) Appl. No.: 18/293,604

(22) PCT Filed: May 18, 2023

(86) PCT No.: PCT/KR2023/006783
§ 371 (c)(1),
(2) Date: Jan. 30, 2024

(87) PCT Pub. No.: WO2024/058339
PCT Pub. Date: Mar. 21, 2024

(65) Prior Publication Data
US 2025/0340504 A1 Nov. 6, 2025

(30) Foreign Application Priority Data
Sep. 14, 2022 (KR) ........................ 10-2022-0115920

(51) Int. Cl.
*C07C 51/377* (2006.01)
*B01D 3/14* (2006.01)
(Continued)

(52) U.S. Cl.
CPC ............ *C07C 51/377* (2013.01); *B01D 3/143* (2013.01); *B01D 3/36* (2013.01); *B01D 11/0488* (2013.01);
(Continued)

(58) Field of Classification Search
CPC ....... C07C 51/377; C07C 51/46; C07C 51/48; C07C 51/09; C07C 51/43; C07C 51/44;
(Continued)

(56) References Cited

U.S. PATENT DOCUMENTS 6,596,901 B1 7/2003 Eck et al.
2017/0253553 A1 9/2017 Kamei et al.
(Continued)

FOREIGN PATENT DOCUMENTS

CN 110099889 A 8/2019
JP 4612123 B2 1/2010
(Continued)

*Primary Examiner* — Deborah D Carr
(74) *Attorney, Agent, or Firm* — Bryan Cave Leighton Paisner LLP

(57) ABSTRACT

A method for preparing acrylic acid, the method including: obtaining a first reaction product including lactic acid, a lactic acid dimer, water, and acrylic acid by supplying a lactic acid aqueous solution to a reactor to allow a dehydration reaction to proceed; supplying the first reaction product to a first cooling tower to separate the first reaction product into a lower fraction of the first cooling tower containing lactic acid and a lactic acid dimer and an upper fraction of the first cooling tower containing water and acrylic acid; obtaining a second reaction product by supplying the lower fraction of the first cooling tower to a lactic acid conversion tank and converting the lactic acid dimer into lactic acid; separating lactic acid from the second reaction product to recover lactic acid; and obtaining acrylic acid by separating acrylic acid from the upper fraction of the first cooling tower.

10 Claims, 2 Drawing Sheets

(51) Int. Cl.

| | |
|---|---|
| ***B01D 3/36*** | (2006.01) |
| ***B01D 11/04*** | (2006.01) |
| ***B01D 17/02*** | (2006.01) |
| ***C07C 51/46*** | (2006.01) |
| ***C07C 51/48*** | (2006.01) |

(52) U.S. Cl.
CPC ...... *B01D 11/0492* (2013.01); *B01D 17/0214* (2013.01); *C07C 51/46* (2013.01); *C07C 51/48* (2013.01)

(58) Field of Classification Search
CPC ....... C07C 51/487; C07C 57/04; B01D 3/143; B01D 3/36; B01D 11/0488; B01D 11/0492; B01D 17/0214
See application file for complete search history.

(56) References Cited

U.S. PATENT DOCUMENTS

| | | | |
|---|---|---|---|
| 2023/0174453 | A1 | 6/2023 | Kim et al. |
| 2023/0271914 | A1 | 8/2023 | Kim et al. |

FOREIGN PATENT DOCUMENTS

| | | | | |
|---|---|---|---|---|
| JP | 2014189510 | A | * | 10/2014 |
| JP | 6272493 | B2 | | 6/2017 |
| KR | 10-1536035 | B1 | | 11/2013 |
| KR | 10-1870503 | B1 | | 6/2018 |
| KR | 10-2022-0071687 | A | | 5/2022 |
| KR | 10-2020071678 | A | | 5/2022 |
| KR | 10-2022-0078233 | A | | 6/2022 |
| KR | 10-2022-0078268 | A | | 6/2022 |
| KR | 10-2022-0078274 | A | | 6/2022 |
| WO | 2013155291 | A1 | | 10/2013 |
| WO | 2013155291 | A4 | | 10/2013 |
| WO | 2015057904 | A1 | | 4/2015 |

* cited by examiner

METHOD FOR PREPARING ACRYLIC ACID

CROSS-REFERENCE TO RELATED APPLICATION

This application is a National Stage Application of International Application No. PCT/KR2023/006783 filed on May 18, 2023, which claims the benefit of priority to Korean Patent Application No. 10-2022-0115920, filed on Sep. 14, 2022, the entire contents of which are incorporated herein by reference.

TECHNICAL FIELD

The present invention relates to a method for preparing acrylic acid, and more particularly, to a method for effectively removing by-products while reducing loss of an unreacted raw material in preparing acrylic acid through a dehydration reaction of lactic acid.

BACKGROUND ART

Acrylic acid is used as a polymer raw material used in fibers, adhesives, paints, fiber processing, leather, construction materials, and the like, and its demand is expanding. In addition, the acrylic acid is also used as a raw material of an absorbent resin, and is widely used industrially for absorbent products such as paper diapers and sanitary napkins, water-retaining agents for agricultural and horticultural use, and waterstops for industrial use.

As a method for preparing acrylic acid according to the related art, a method of air oxidizing propylene is generally used, but this method is a method for preparing acrylic acid by converting propylene into acrolein by a gas-phase catalytic oxidation reaction, and subjecting the acrolein to a gas-phase catalytic oxidation reaction, and in this case, acetic acid is produced as a by-product, which is difficult to separate from acrylic acid. In addition, the method for preparing acrylic acid using propylene uses, as a raw material, propylene obtained by refining crude oil, which is a fossil resource, and has problems in terms of raw material costs or environmental pollution considering problems such as the recent rise in crude oil prices or global warming.

Accordingly, studies on a method for preparing acrylic acid from a carbon-neutral biomass raw material have been conducted. For example, there is a method for preparing acrylic acid (AA) through a gas-phase dehydration reaction of lactic acid (LA). This method is a method for preparing acrylic acid through an intramolecular dehydration reaction of lactic acid generally at a high temperature of 300° C. or higher in the presence of a catalyst. A reaction product including acrylic acid is produced through the dehydration reaction of lactic acid, and unreacted lactic acid is included in the reaction product according to a conversion rate. In a case where unreacted lactic acid is included in the reaction product, the economic efficiency of the process can be improved only when the unreacted lactic acid is recovered in a separation process. However, an oligomerization reaction of the lactic acid proceeds rapidly at a high concentration and a high temperature, and it is difficult to recover the lactic acid.

BRIEF DESCRIPTION

Technical Problem

In order to solve the problems mentioned in the background art, an object of the present invention is to provide a method for saving energy consumption by effectively separating unreacted lactic acid from a reaction product produced in preparing acrylic acid through a dehydration reaction of lactic acid, and efficiently recovering unreacted lactic acid by converting a lactic acid dimer produced by an oligomerization reaction of lactic acid into lactic acid.

Technical Solution

In one general aspect, a method for preparing acrylic acid includes: obtaining a first reaction product including lactic acid, a lactic acid dimer, water, and acrylic acid by supplying a lactic acid aqueous solution to a reactor to allow a dehydration reaction to proceed; supplying the first reaction product to a first cooling tower to separate the first reaction product into a lower fraction of the first cooling tower containing lactic acid and a lactic acid dimer and an upper fraction of the first cooling tower containing water and acrylic acid; obtaining a second reaction product by supplying the lower fraction of the first cooling tower to a lactic acid conversion tank and converting the lactic acid dimer into lactic acid; separating lactic acid from the second reaction product to recover lactic acid; and obtaining acrylic acid by separating acrylic acid from the upper fraction of the first cooling tower.

Advantageous Effects

According to the method for preparing acrylic acid of the present invention, unreacted lactic acid is separated in advance before distillation of the reaction product including acrylic acid, such that energy costs can be reduced compared to the case of separating unreacted lactic acid after distillation.

Furthermore, as the lactic acid dimer included in the reaction product is converted into lactic acid, the amount of lactic acid lost in the form of a lactic acid dimer is minimized, such that a recovery rate of unreacted lactic acid can be improved and economic efficiency of the process can be improved.

In addition, the acrylic acid aqueous solution discharged from the cooling tower is divided and supplied to an extraction column and an azeotropic distillation column, such that energy consumption required for distillation of water in the azeotropic distillation column can be saved, and at the same time, loss of acrylic acid can be reduced and high-purity acrylic acid can be obtained.

DETAILED DESCRIPTION

Figure 1:
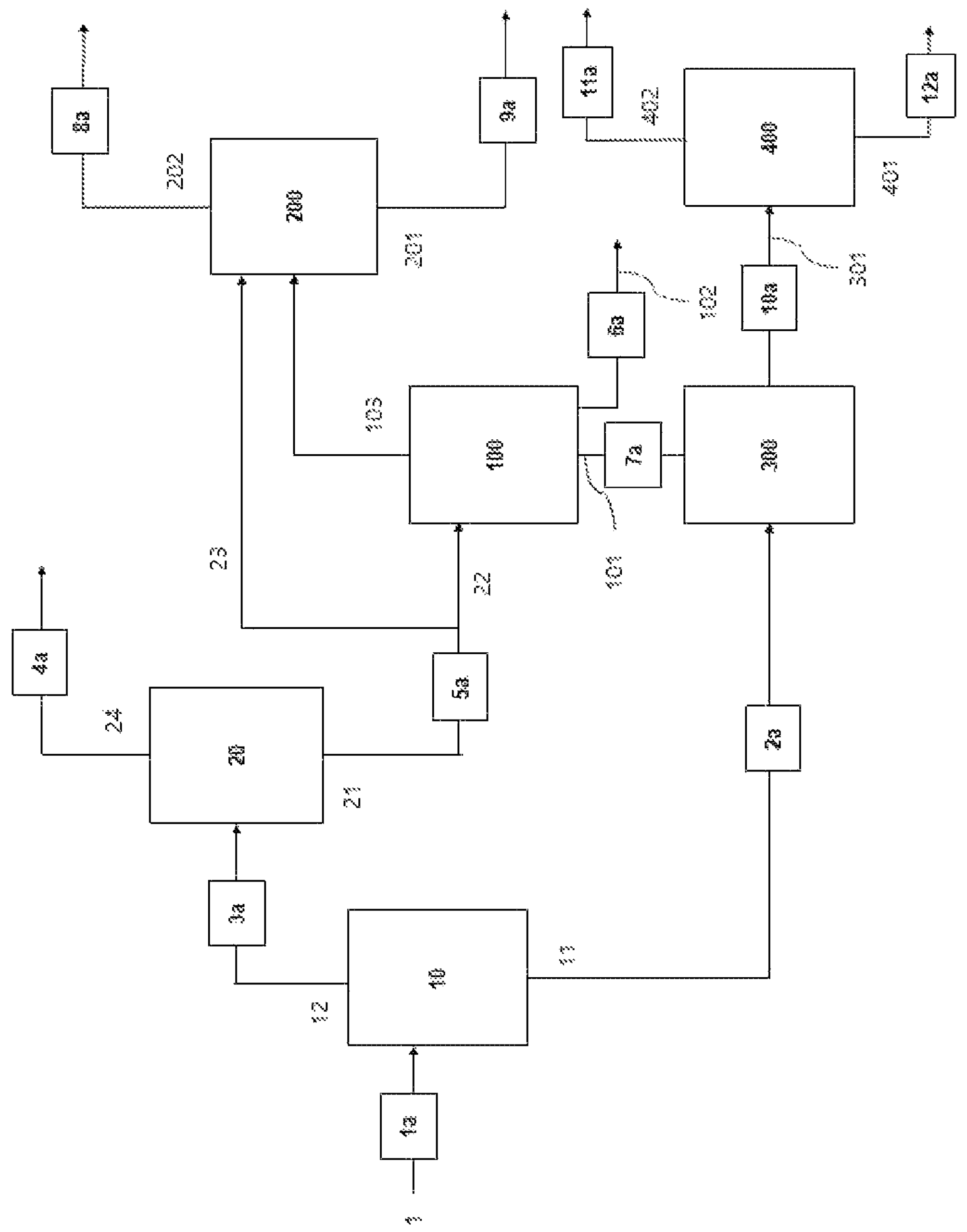
FIG. 1 is a process flow chart according to a method for preparing acrylic acid in an exemplary embodiment of the present invention.

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention can refer to a flow of a fluid in a process, or can refer to a fluid itself flowing in a pipe. Specifically, the stream can refer to both a fluid itself flowing in a pipe connecting respective devices to each other and a flow of a fluid. In addition, the fluid can refer to a gas or liquid, and a case of the fluid including a solid component is not excluded.

Meanwhile, in the present invention, in devices such as a cooling tower, an extraction column, and a distillation column, the "lower portion" of the device refers to a point at a height of 95% to 100% from the top of the device to the bottom, unless otherwise specified, and specifically, can refer to the bottom (of the tower). Similarly, the "upper portion" of the device refers to a point at a height of 0% to 5% from the top of the device to the bottom, unless otherwise specified, and specifically, can refer to the top (of the tower).

In addition, unless otherwise specified, an operating temperature of the cooling tower in the present invention can refer to an operating temperature at the lower portion of the cooling tower, and an operating pressure of the cooling tower can refer to an operating pressure at the upper portion of the cooling tower.

Hereinafter, each process that can be included in exemplary embodiments of the present invention will be described with reference to FIG. 1 and the like.

A method for preparing acrylic acid according to an exemplary embodiment of the present invention can include: obtaining a first reaction product including lactic acid, a lactic acid dimer, water, and acrylic acid by supplying a lactic acid aqueous solution to a reactor to allow a dehydration reaction to proceed; supplying the first reaction product to a first cooling tower to separate the first reaction product into a lower fraction of the first cooling tower containing lactic acid and a lactic acid dimer and an upper fraction of the first cooling tower containing water and acrylic acid; obtaining a second reaction product by supplying the lower fraction of the first cooling tower to a lactic acid conversion tank and converting the lactic acid dimer into lactic acid; separating lactic acid from the second reaction product to recover lactic acid; and obtaining acrylic acid by separating acrylic acid from the upper fraction of the first cooling tower.

First, the method for preparing acrylic acid according to an exemplary embodiment of the present invention can include obtaining a first reaction product including lactic acid, a lactic acid dimer, water, and acrylic acid by supplying a lactic acid aqueous solution to a reactor to allow a dehydration reaction to proceed.

Specifically, as a method for preparing acrylic acid according to the related art, a method of air oxidizing propylene is generally used, but this method is a method for preparing acrylic acid by converting propylene into acrolein by a gas-phase catalytic oxidation reaction, and subjecting the acrolein to a gas-phase catalytic oxidation reaction, and in this case, acetic acid is produced as a by-product, which is difficult to separate from acrylic acid. In addition, the method for preparing acrylic acid using propylene uses, as a raw material, propylene obtained by refining crude oil, which is a fossil resource, and has problems in terms of raw material costs or environmental pollution considering problems such as the recent rise in crude oil prices or global warming.

In order to solve the problems of the method for preparing acrylic acid according to the related art, studies on a method for preparing acrylic acid from a carbon-neutral biomass raw material have been conducted. For example, there is a method for preparing acrylic acid (AA) through a gas-phase dehydration reaction of lactic acid (LA). This method is a method for preparing acrylic acid through an intramolecular dehydration reaction of lactic acid generally at a high temperature in the presence of a catalyst. A reaction product including acrylic acid is produced through the dehydration reaction of lactic acid, and unreacted lactic acid is included in the reaction product according to a conversion rate. In a case where unreacted lactic acid is included in the reaction product, the economic efficiency of the process can be improved only when the unreacted lactic acid is recovered in a separation process. However, an oligomerization reaction of the lactic acid proceeds rapidly at a high concentration and a high temperature, and it is difficult to recover the lactic acid. Furthermore, in a case where an additional distillation column or the like to recover lactic acid is provided, the overall process cost increases because a lot of energy is required for operation.

Accordingly, in order to solve the problems in the related art, the present invention is intended to provide a method capable of improving a recovery rate of unreacted lactic acid and reducing costs for equipment such as an additional distillation device for separating lactic acid in a subsequent process and operating costs for its operation by separating lactic acid from a reaction product including acrylic acid produced through a dehydration reaction of lactic acid in advance before a distillation process so that the time when lactic acid at a high concentration is exposed to a high temperature is shortened to minimize oligomerization of lactic acid.

In addition, an object of the present invention is to provide a method capable of further improving a recovery rate of unreacted lactic acid by converting a lactic acid dimer that can be produced by an oligomerization reaction of lactic acid in the dehydration reaction into lactic acid again.

According to an exemplary embodiment of the present invention, a first reaction product including acrylic acid can be produced by supplying a lactic acid aqueous solution to a reactor in advance and allowing a dehydration reaction to proceed. In this case, the dehydration reaction can be performed as a gas phase reaction in the presence of a catalyst. For example, a concentration of lactic acid in the lactic acid aqueous solution can be 10 wt % or more, 20 wt % or more, or 30 wt % or more, and 40 wt % or less, 50 wt % or less, 60 wt % or less, or 70 wt % or less. When the lactic acid is present at a high concentration, oligomers of lactic acid can be excessively formed by an equilibrium reaction between lactic acid and a lactic acid dimer, and therefore, lactic acid can be used in the form of an aqueous solution at a concentration within the above range.

The reactor can include a reactor capable of dehydrating normal lactic acid, the reactor can include a reaction tube filled with a catalyst, and acrylic acid can be produced by dehydrating lactic acid by a gas-phase catalytic reaction while passing a reaction gas including volatile components of a lactic acid aqueous solution as a raw material through the reaction tube. In addition to lactic acid, the reaction gas can further include one or more diluent gases selected from water vapor, nitrogen, and air for concentration adjustment.

The operation of the reactor can be performed under normal lactic acid dehydration reaction conditions. In this case, an operating temperature of the reactor can refer to a set temperature of a heat medium or the like used for temperature control of the reactor.

The catalyst used in the dehydration reaction of lactic acid can include, for example, one or more selected from the group consisting of a sulfate-based catalyst, a phosphate-based catalyst, and a nitrate-based catalyst. As specific examples, the sulfate can include $Na_2SO_4$, $K_2SO_4$, $CaSO_4$, and $Al_2(SO_4)_3$, the phosphate can include $Na_3PO_4$, $Na_2HPO_4$, $NaH_2PO_4$, $K_3PO_4$, $K_2HPO_4$, $KH_2PO_4$, $CaHPO_4$, $Ca_3(PO_4)_2$, $AlPO_4$, $CaH_2P_2O_7$, and $Ca_2P_2O_7$, and the nitrate can include $NaNO_3$, $KNO_3$, and $Ca(NO_3)_2$. In addition, the catalyst can be supported on a support. Examples of the support include one or more selected from the group consisting of diatomite, alumina, silica, titanium dioxide, carbide, and zeolite.

The first reaction product produced through the dehydration reaction of lactic acid can include lactic acid, a lactic acid dimer, and water ($H_2O$) in addition to acrylic acid, which is a desired product, and can also include light gas components and heavy by-products (heavies). Here, the lactic acid can be unreacted lactic acid, and the lactic acid dimer can be a by-product produced by an oligomerization reaction of unreacted lactic acid in the dehydration reaction. Meanwhile, the heavy by-products collectively refer to by-products having a higher boiling point than acrylic acid and lactic acid other than lactic acid dimer, and for example, can include 3,4-dimethyl-2,5-furandione ($C_6H_6O_3$).

The method for preparing acrylic acid through a dehydration reaction of lactic acid can secure raw material competitiveness compared to the method of air oxidizing propylene according to the related art and can solve the problem of environmental pollution, but a conversion rate of lactic acid is low, and various by-products are produced, resulting in a low yield of acrylic acid. Therefore, development of a process for improving economic efficiency is demanded. Accordingly, the present invention can provide a method for improving economic efficiency by reducing overall equipment costs and energy costs as well as increasing a recovery rate of unreacted lactic acid.

The method for preparing acrylic acid according to an exemplary embodiment of the present invention can include supplying the first reaction product to a first cooling tower to separate the first reaction product into a lower fraction of the first cooling tower containing lactic acid and a lactic acid dimer and an upper fraction of the first cooling tower containing water and acrylic acid.

Specifically, a reactor discharge stream 1 containing the first reaction product is a gaseous stream, and the reactor discharge stream 1 can be supplied to the first cooling tower 10 to be cooled. That is, lactic acid, a lactic acid dimer, and a heavy by-product having a relatively high boiling point in the first reaction product supplied to the first cooling tower 10 are cooled and condensed to form a liquid condensate, and can be separated into the lower fraction of the first cooling tower 10. Meanwhile, acrylic acid, water, and a light gas component having a relatively low boiling point in the reaction product can be separated into the upper fraction of the first cooling tower 10 as gaseous phases. Here, the light gas component is a component having a lower boiling point than water, and specifically, can include carbon monoxide, carbon dioxide, and acetaldehyde in addition to the diluent gas.

Lactic acid included in the first reaction product is separated in advance by cooling, such that deformation of lactic acid due to exposure to a high temperature, for example, oligomerization, can be prevented to increase a recovery rate of lactic acid, and the recovered lactic acid can be efficiently reused as a raw material for the dehydration reaction for preparing acrylic acid. In addition, since there is no need to provide an additional distillation device or the like for separating and recovering lactic acid in a subsequent process, energy costs for operating the distillation device can be reduced. Furthermore, unreacted lactic acid is separated before an azeotropic distillation process described below, such that energy consumption required for azeotropic distillation can be saved.

To this end, an operating temperature of the first cooling tower 10 can be 100° C. or higher, 110° C. or higher, or 120° C. or higher, and 180° C. or lower, 170° C. or lower, or 160° C. or lower. When the temperature is lower than 100° C., components other than unreacted lactic acid can be excessively condensed, and the purity of the recovered lactic acid is reduced, which can cause loss of acrylic acid, which is a desired product. On the other hand, when the temperature exceeds 180° C., unreacted lactic acid is not sufficiently condensed, which can cause discharge of unreacted lactic acid through the upper discharge of the first cooling tower 10, and as a result, a recovery rate of lactic acid can be reduced, and it can be difficult to obtain high-purity acrylic acid.

In addition, an operating pressure of the first cooling tower 10 can be 1 $kg/cm^2$ or more, 1.5 $kg/cm^2$ or more, or 1.8 $kg/cm^2$ or more, and 20 $kg/cm^2$ or less, 10 $kg/cm^2$ or less, or 5 $kg/cm^2$ or less. When the pressure is high, a volumetric flow rate is reduced, resulting in a reduction in cost of the cooling tower, but dimers of lactic acid and acrylic acid can be produced due to an increase in operating temperature of the cooling tower, and therefore, it is required to set an appropriate operating pressure at which a dimer is not produced.

When the operating conditions of the first cooling tower 10 are controlled to the operating temperature and the operating pressure within the above ranges, compositions of a lower discharge stream and an upper discharge stream of the first cooling tower 10 can be controlled, and through this, a composition of an acrylic acid aqueous solution stream discharged through the lower discharge of the second cooling tower 20 can be easily controlled.

From this point of view, the upper fraction discharged from the first cooling tower may not contain unreacted lactic acid, and even when unreacted lactic acid is contained, unreacted lactic acid may be present in an amount of 5 wt % or less, and specifically, 3 wt % or less.

Meanwhile, a ratio of a flow rate of water in the stream discharged through the lower discharge of the first cooling tower to a flow rate (kg/hr) of water included in the reaction product introduced into the first cooling tower 10 can be 15 wt % or less, and a ratio of a flow rate of acrylic acid in the stream discharged through the lower discharge of the first cooling tower to a flow rate (kg/hr) of acrylic acid included in the reaction product introduced into the first cooling tower 10 can be 15 wt % or less.

Meanwhile, the upper fraction of the first cooling tower 10 containing water and acrylic acid, specifically, the upper fraction of the first cooling tower 10 containing water, acrylic acid, and a light gas component can be discharged as an upper discharge stream 12 of the first cooling tower and can be introduced into an acrylic acid purification process. The acrylic acid purification process is a process of obtaining high-purity acrylic acid at a high concentration by separating acrylic acid from other components. Meanwhile, the lower fraction of the first cooling tower 10 including lactic acid and a lactic acid dimer, specifically, the lower fraction of the first cooling tower 10 including lactic acid, a lactic acid dimer, and a heavy by-product can be discharged as a lower discharge stream 11 of the first cooling tower and can be supplied to a lactic acid conversion tank 300. An equilibrium reaction, in which a lactic acid dimer is converted into lactic acid, occurs in the lactic acid conversion tank 300, and through this, loss of lactic acid in the form of a lactic acid dimer can be prevented as much as possible.

Meanwhile, according to an exemplary embodiment of the present invention, a process of supplying the upper discharge stream 12 of the first cooling tower to the second cooling tower 20 before introducing the upper discharge stream 12 of the first cooling tower into an acrylic acid purification process to remove the light gas component contained in the upper discharge stream 12 of the first cooling tower can be performed. Specifically, the upper discharge stream 12 of the first cooling tower is supplied to the second cooling tower 20 to be additionally cooled, such that the upper discharge stream 12 can be separated into a lower fraction containing water and acrylic acid and an upper fraction containing a light gas component.

An operating temperature of the second cooling tower 20 can be 60° C. or higher, 80° C. or higher, or 100° C. or higher, and 140° C. or lower, 130° C. or lower, or 120° C. or lower, and an operating pressure of the second cooling tower 20 can be 0.8 $kg/cm^2$ or more, 1.0 $kg/cm^2$ or more, or 1.3 $kg/cm^2$ or more, and 20 $kg/cm^2$ or less, 10 $kg/cm^2$ or less, or 5 $kg/cm^2$ or less. When the operating conditions of the second cooling tower 20 are controlled to the operating temperature and the operating pressure within the above ranges, a composition of a light gas component separated through an upper discharge stream 24 of the second cooling tower 20 is controlled, such that the loss of acrylic acid can be minimized, a light gas component containing a diluent gas and acetaldehyde can be removed out of the system, and a composition of an acrylic acid aqueous solution stream 21 containing acrylic acid and water discharged through the lower of the second cooling tower 20 can be controlled.

In the method for preparing acrylic acid according to the related art, even when a cooling tower is used, the cooling tower is used for cooling the gaseous reaction product so that the gaseous reaction product is appropriately introduced into an acrylic acid purification process, and is not a cooling tower used for material separation. This is because it is difficult to recover a material with a desired purity when the material is separated by cooling. However, in the present invention, the cooling amount of the cooling tower is controlled to adjust the amount of components to be cooled, such that the material separation effect can also be obtained, in addition to cooling of the reaction product, which is the original object of the present invention.

Subsequently, the acrylic acid aqueous solution stream, specifically, the upper discharge stream 12 of the first cooling tower 10 containing water and acrylic acid, or the lower discharge stream 21 of the second cooling tower 20 when the upper discharge stream of the first cooling tower 10 is additionally cooled in the second cooling tower 20, can be introduced into a purification process for obtaining acrylic acid. The purification process is a process for obtaining high-purity acrylic acid from water and some impurities in the acrylic acid aqueous solution, and the obtained acrylic acid should be recovered with high purity, and energy consumption involved in the process should be saved in consideration of economic efficiency.

For example, the purification process can be performed by an extraction process of separating the acrylic acid aqueous solution into an extract containing acrylic acid and an extraction solvent and a raffinate containing water using an extraction solvent in an extraction column. However, when the purification process is performed by an extraction process, although energy consumption can be more reduced than in the distillation process, it can be difficult to obtain high-purity acrylic acid because some by-products to be removed together with water are contained in the extract.

Meanwhile, as another example of the purification process, the purification process can be performed by an azeotropic distillation process. In this case, on the premise of using an azeotropic solvent, the separation efficiency between water and acrylic acid is higher than in a simple extraction process, and thus, high-purity acrylic acid can be obtained, but excessive energy consumption is required due to accompanying distillation of water having a high specific heat, which can be less preferable in terms of economic efficiency.

Therefore, according to an exemplary embodiment of the present invention, the purification process can be performed in combination with the extraction process and the azeotropic distillation process by supplying a part of the acrylic acid aqueous solution stream obtained according to the cooling process performed by the first cooling tower or the first and second cooling towers to an extraction column 100 as a first acrylic acid aqueous solution stream 22, and supplying a remainder to an azeotropic distillation column 200 as a second acrylic acid aqueous solution stream 23. That is, the acrylic acid aqueous solution stream 21 is divided and supplied to the extraction column 100 and the azeotropic distillation column 200, such that energy consumption in a subsequent process can be saved, and by-products that can be partially contained in the acrylic acid aqueous solution stream 21 can be efficiently separated.

Specifically, a ratio of a flow rate of the first acrylic acid aqueous solution stream 22 supplied to the extraction column to the total flow rate of the first acrylic acid aqueous solution stream 21 before branching, that is, the first acrylic acid aqueous solution stream and the second acrylic acid aqueous solution stream after branching, can be 30 wt % to 70 wt %, and specifically, 40 wt % to 50 wt %. When the flow rate ratio is 30 wt % or more, the flow rate introduced into the azeotropic distillation column 200 is reduced, and the amount of energy consumed in distilling water having a high specific heat in the azeotropic distillation column 200 can be reduced. Meanwhile, when the flow rate ratio is 70 wt % or less, by-products can be efficiently separated through the upper discharge of the azeotropic distillation column 200, such that accumulation of the by-products in the system can be prevented, high-purity acrylic acid can also be obtained, the amount of extractant required for removing water in the extraction column 100 can be reduced, a flow rate of the extractant introduced into the azeotropic distillation column 200 can be reduced to reduce the amount of energy consumed in distillation, and the by-products can be efficiently separated, thereby obtaining high-purity acrylic acid.

Meanwhile, the extraction column 100 removes most of the water contained in the first acrylic acid aqueous solution stream 22 without using a lot of energy and supplies the first acrylic acid aqueous solution stream 22 from which water is mostly removed to the azeotropic distillation column 200, such that energy used for azeotropic distillation in the azeotropic distillation column 200 described below can be reduced. In this respect, it is preferable that, in the extraction in the extraction column 100, the extraction solvent comes into contact with the stream supplied from the extraction column by a liquid-liquid contact method from the viewpoint of improving the energy efficiency of the entire process.

In this case, the extraction solvent can be a hydrocarbon-based solvent that can form an azeotrope with water and does not form an azeotrope with acrylic acid, but can sufficiently extract acrylic acid, and it is advantageous in the extraction process that the extraction solvent has a boiling point of 10 to 120° C. Specifically, the extraction solvent can be one or more solvents selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

In addition, as the extraction column 100, an extraction device based on a liquid-liquid contact method can be used. Non-limiting examples of the extraction device include a Karr reciprocating plate column, a rotary-disk contactor, a Scheibel column, a Kuhni column, a spray extraction tower, a packed extraction tower, a pulsed packed column, a mixer-settler bank, a mixer, and a centrifuge (centrifugal counter current extractor).

With such a method, water in the acrylic acid aqueous solution stream supplied to the extraction column 100 can be significantly removed, an extract containing an extraction solvent and acrylic acid can be obtained, and the extract can be supplied to the azeotropic distillation column 200 as an upper discharge stream 103 of the extraction column.

In addition, water contained in the acrylic acid aqueous solution stream can be recovered as a raffinate by the extraction process. It is common to discharge the raffinate as wastewater in the related art, but in the present invention, after the raffinate is discharged from the extraction column, a part 101 is introduced into the lactic acid conversion tank 300, and the raffinate can perform a function of adjusting an equilibrium reaction so that the equilibrium reaction of the lactic acid dimer to lactic acid is promoted by water contained in the raffinate. A remainder 102 can be discharged out of the system as wastewater. As a result, it is possible to achieve an effect of reducing the amount of wastewater discharged compared to the case of discharging all of the raffinate out of the system in the related art. Furthermore, as water is recovered in the extraction process as described above, the energy consumption can be significantly saved by reducing an operating load of a distillation process described below.

Subsequently, according to an exemplary embodiment of the present invention, the second acrylic acid aqueous solution stream 23 and the upper discharge stream 103 of the extraction column can be supplied to the azeotropic distillation column 200, and a distillation process for these streams can be performed. The distillation process in the azeotropic distillation column 200 for the stream supplied to the azeotropic distillation column 200 can be a process of separating the stream into an upper fraction containing water and an extraction solvent and a lower fraction containing acrylic acid by azeotropic distillation.

According to the present invention, it is advantageous in terms of process that the distillation in the azeotropic distillation column 200 is performed in the presence of an azeotropic solvent. Here, the azeotropic solvent is a hydrophobic solvent that can form an azeotrope with water and does not form an azeotrope with acrylic acid, and any hydrocarbon-based solvent that satisfies the physical properties can be used without limitation. In addition, the azeotropic solvent can have a boiling point lower than that of acrylic acid, and preferably, can have a boiling point of 10 to 120° C.

According to the present invention, the azeotropic solvent that satisfies the physical properties can be one or more solvents selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

In addition, the azeotropic solvent can be the same as or different from the extract solvent applied to the extraction column 100. However, considering production efficiency and the like according to a continuous process, the azeotropic solvent is preferably the same as the extraction solvent. As described above, when the same compound is used as the azeotropic solvent and the extraction solvent, at least a part of the azeotropic solvent distilled and recovered in the azeotropic distillation column 200 can be supplied to the extraction column 100 and used as a part of the extraction solvent.

When the azeotropic solvent is added to the azeotropic distillation column 200 as described above, the azeotrope of acrylic acid and water is broken. Accordingly, water supplied to the azeotropic distillation column 200 and the azeotropic solvent used in the azeotropic distillation can form an azeotrope together and can be recovered through an upper fraction of the azeotropic distillation column 200. In addition, a lower fraction 201 containing acrylic acid can be recovered through the lower of the azeotropic distillation column 200.

The upper fraction thus recovered of the azeotropic distillation column can be supplied to a layer separator through an upper discharge stream 202 of the azeotropic distillation column. The layer separator is a liquid-liquid layer separator and is a device for separating immiscible fluids using gravity or centrifugal force based on a density difference. A relatively light liquid can be separated through the upper of the layer separator, and a relatively heavy liquid can be separated through the lower of the layer separator. Specifically, the upper discharge stream 202 of the azeotropic distillation column supplied to the layer separator can be separated into an organic layer including an azeotropic solvent and a water layer including water.

In addition, the organic layer separated in the layer separator is discharged through a discharge stream of the layer separator, and the discharge stream of the layer separator containing an azeotropic solvent or an extraction solvent can be circulated to one or more of the extraction column and the azeotropic distillation column to be reused as an azeotropic solvent or an extraction solvent.

Meanwhile, the method for preparing acrylic acid according to an exemplary embodiment of the present invention can include obtaining a second reaction product by supplying the lower fraction of the first cooling tower to a lactic acid conversion tank and converting the lactic acid dimer into lactic acid.

Specifically, the lower fraction of the first cooling tower containing lactic acid and a lactic acid dimer can be discharged as the lower discharge stream 11 of the first cooling tower and then can be supplied to the lactic acid conversion tank 300, and in the lactic acid conversion tank 300, the lactic acid dimer can be converted into lactic acid using a reverse reaction of an equilibrium reaction between lactic acid and a lactic acid dimer as represented by the following Reaction Formula 1.

[Reaction Formula 1]

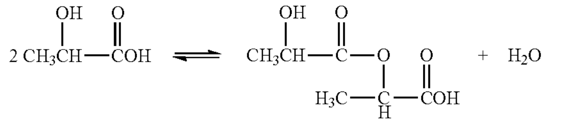

Referring to Reaction Formula 1, in the lactic acid conversion tank 300, an equilibrium reaction in which a forward reaction in which lactic acid is converted into a lactic acid dimer and water and a reverse reaction in which a lactic acid dimer reacts with water and is converted into lactic acid are performed together can occur. Here, water is additionally supplied to the lactic acid conversion tank 300 to increase a concentration of the reactant of the reverse reaction, such that the reverse reaction in which a lactic acid dimer is converted into lactic acid can be promoted. Therefore, the lactic acid dimer contained in the lower discharge stream 11 of the first cooling tower can be converted into lactic acid as much as possible, thereby preventing unreacted lactic acid from being lost in the form of a lactic acid dimer and increasing a recovery rate of lactic acid.

Meanwhile, water supplied to the lactic acid conversion tank 300 can be water separated in the acrylic acid purification process described above. The acrylic acid purification process involves a process of separating acrylic acid from the acrylic acid aqueous solution containing acrylic acid and water, and for example, streams containing water can be separated and discharged from the extraction column 100 and the azeotropic distillation column 200 in the acrylic acid purification process. These streams containing water can be supplied to the lactic acid conversion tank 300 and can be used for the equilibration reaction.

According to an exemplary embodiment of the present invention, in the extraction process performed in the extraction column 100, the raffinate containing water can be discharged through the lower of the extraction column, and the part 101 of the stream can be supplied to the lactic acid conversion tank 300. Meanwhile, the raffinate contains 95 wt % or more of water, and as water contained in the raffinate is supplied to the lactic acid conversion tank 300, a reaction of a lactic acid dimer to lactic acid can be promoted in the lactic acid conversion tank 300.

Meanwhile, a flow rate of the raffinate that is discharged through the lower of the extraction column 100 and is supplied to the lactic acid conversion tank 300 can be determined by a relationship between a content of lactic acid and a lactic acid dimer and a content of water in the lactic acid conversion tank 300. That is, when the content of water in the lactic acid conversion tank 300 is too low, the reaction of a lactic acid dimer to lactic acid is not performed smoothly, which increases the amount of lactic acid lost in the form of a lactic acid dimer. In addition, when the content of water in the lactic acid conversion tank 300 is too high, lactic acid can be sufficiently converted from a lactic acid dimer, but the amount of energy required in separating lactic acid and water in a lactic acid purification column 400 increases. From this point of view, the content of water in the lactic acid conversion tank 300 is preferably maintained at 60 to 70 wt % with respect to the total weight of the components in the lactic acid conversion tank. Furthermore, a lower discharge stream of the extraction column 100 can be supplied to the lactic acid conversion tank 300 at a flow rate at which the content of water in the above range can be maintained.

Due to the conversion of the lactic acid dimer into lactic acid, a content of lactic acid included in the second reaction product is higher than a content of lactic acid contained in the stream supplied to the lactic acid conversion tank 300, for example, the lower discharge stream 11 of the first cooling tower. Specifically, a mass flow rate of lactic acid included in the second reaction product discharged from the lactic acid conversion tank 300 can be increased by 5 wt % to 20 wt % compared to a mass flow rate of lactic acid contained in the lower discharge stream 11 of the first cooling tower.

Meanwhile, according to an exemplary embodiment of the present invention, the second reaction product discharged from the lactic acid conversion tank 300 can be supplied to the lactic acid purification column 400 as a discharge stream 301 of the lactic acid conversion tank.

Lactic acid and water included in the second reaction product can be separated in the lactic acid purification column 400, and the separated lactic acid and water can be circulated through upper discharge stream 402 of the lactic acid purification column 400 to the reactor to be reused as a raw material for the dehydration reaction of lactic acid performed in the reactor. Meanwhile, components other than lactic acid and water, for example, components of a lactic acid dimer and a heavy by-product can be discharged as stream 401 through the lower of the lactic acid purification column 400 and discharged out of the system.

Hereinabove, the method for preparing acrylic acid according to the present invention has been described and illustrated in the drawings. However, the description and the illustration of the drawings are for only essential components for understating the present invention, and processes and devices not separately described and illustrated can be properly applicable and used for implementing the method for preparing acrylic acid according to the present invention, in addition to the processes and devices described and illustrated in the drawings.

Hereinafter, the present invention will be described in more detail by Examples. However, the following Examples are provided for illustrating the present invention. It is apparent to those skilled in the art that various modifications and alterations can be made without departing from the scope and spirit of the present invention, and the scope of the present invention is not limited thereto.

EXAMPLES

Example 1

According to the process flow chart illustrated in FIG. 1, the acrylic acid producing process was simulated using Aspen Plus simulator available from Aspen Technology, Inc.

Specifically, 30 wt % of a lactic acid aqueous solution and nitrogen ($N_2$) as a diluent gas were supplied to a reactor, and a first reaction product including lactic acid, a lactic acid dimer, water, and acrylic acid was produced through a dehydration reaction.

A reactor discharge stream containing the first reaction product was supplied to a first cooling tower 10. In the first cooling tower 10, the reactor discharge stream was cooled and condensed, and then separated into a lower discharge stream 11 of the first cooling tower containing lactic acid and a lactic acid dimer and an upper discharge stream 12 of the first cooling tower containing a light gas component, water, and acrylic acid. At this time, a lower operating temperature and an upper operating pressure of the first cooling tower 10 were controlled to 125° C. and 1.9 kg/$cm^2$, respectively.

Subsequently, the lower discharge stream 11 of the first cooling tower was introduced into a lactic acid conversion tank 300. Meanwhile, the upper discharge stream 12 of the first cooling tower was supplied to a second cooling tower 20 and then cooled and condensed, such that the upper discharge stream 12 of the first cooling tower was separated into a lower discharge stream 21 of the second cooling tower containing water and acrylic acid and an upper discharge stream 24 of the second cooling tower containing a light gas component including nitrogen. At this time, a lower operating temperature and an upper operating pressure of the second cooling tower 20 were controlled to 107° C. and 1.3 kg/$cm^2$, respectively.

A part of the lower discharge stream 21 of the second cooling tower was supplied to an extraction column 100 as a first acrylic acid aqueous solution stream 22, a remainder was supplied to an azeotropic distillation column 200 as a second acrylic acid aqueous solution stream 23, and a ratio of a mass flow rate of the first acrylic acid aqueous solution stream 22 supplied to the extraction column 100 to a flow rate of the lower discharge stream 21 of the second cooling tower was maintained at 50 wt %.

Meanwhile, in the extraction column 100, acrylic acid was dissolved using toluene as an extraction solvent, and then an extract containing acrylic acid and an extraction solvent was separated through an upper discharge stream 103 of the extraction column 100 and supplied to the azeotropic distillation column 200, and a part 101 of a lower discharge stream of the extraction column 100 containing water was supplied to the lactic acid conversion tank 300.

In addition, distillation was performed in the azeotropic distillation column 200 to which the second acrylic acid aqueous solution stream 23 and the upper discharge stream 103 of the extraction column 100 were supplied, such that acrylic acid was obtained through the lower discharge stream 210, and a stream 202 containing water and an extraction solvent was discharged through the upper. Subsequently, the stream containing water and an extraction solvent was supplied to a layer separator to separate the stream into water and an extraction solvent, water was discharged out of the system, and the extraction solvent was separately circulated to the extraction column 100 and the azeotropic distillation column 200.

Meanwhile, an oligomerization reaction of lactic acid and a reverse reaction thereof were performed in the lactic acid conversion tank 300 to convert a part of the lactic acid dimer into lactic acid, thereby obtaining a second reaction product. The obtained second reaction product was supplied to a lactic acid purification column 400 and distilled, thereby recovering unreacted lactic acid through the upper discharge stream 402 of the lactic acid purification column 400.

In this case, the flow rate (kg/hr) and composition (wt %) of each component in each stream 1a through 12a of FIG. 1 are shown in Table 1.

TABLE 1

| Component | Unit | 1a | 2a | 3a | 4a | 5a | 6a | 7a | 8a | 9a | 10a | 11a | 12a |
|---|---|---|---|---|---|---|---|---|---|---|---|---|---|
| Flow rate | | 11000 | 1409 | 9592 | 1023 | 8568 | 2343 | 650 | 3964 | 1611 | 2058 | 1903 | 155 |
| $N_2$ | kg/hr | 1000 | 0 | 1000 | 1000 | 0 | 0 | 0 | 0 | 0 | 0 | 0 | 0 |
| Lactic acid | kg/hr | 600 | 490 | 74 | 0 | 74 | 24 | 7 | 0 | 44 | 515 | 510 | 5 |
| Water | kg/hr | 7504 | 572 | 6936 | 22 | 6914 | 2309 | 640 | 3964 | 0 | 1210 | 1210 | 0 |
| Acrylic acid | kg/hr | 1728 | 181 | 1547 | 1 | 1546 | 4 | 1 | 0 | 1541 | 182 | 182 | 0 |
| Heavy component | kg/hr | 168 | 133 | 35 | 0 | 35 | 6 | 2 | 0 | 27 | 135 | 1 | 134 |
| Lactic acid dimer | kg/hr | 0 | 33 | 0 | 0 | 0 | 0 | 0 | 0 | 0 | 16 | 0 | 16 |
| Composition | | | | | | | | | | | | | |
| $N_2$ | wt % | 9% | 0% | 10% | 98% | 0% | 0% | 0% | 0% | 0% | 0% | 0% | 0% |
| Lactic acid | wt % | 5% | 35% | 1% | 0% | 1% | 1% | 1% | 0% | 3% | 25% | 27% | 3% |
| Water | wt % | 68% | 41% | 72% | 2% | 81% | 99% | 99% | 100% | 0% | 59% | 64% | 0% |
| Acrylic acid | wt % | 16% | 13% | 16% | 0% | 18% | 0% | 0% | 0% | 96% | 9% | 10% | 0% |
| Heavy component | wt % | 2% | 9% | 0% | 0% | 0% | 0% | 0% | 0% | 2% | 7% | 0% | 87% |
| Lactic acid dimer | wt % | 0% | 2% | 0% | 0% | 0% | 0% | 0% | 0% | 0% | 1% | 0% | 10% |

As shown in Table 1 and FIG. 1, it could be confirmed that the recovery rate of lactic acid was 85% with reference to the mass flow rate (510 kg/hr) of lactic acid recovered through the stream No. 11a compared to the mass flow rate (600 kg/hr) of lactic acid introduced through the stream No. 1a. Furthermore, when the streams before and after being introduced into the lactic acid conversion tank 300 were compared with each other, it could be confirmed that lactic acid was increased by 5.1% by the reverse reaction of the oligomerization reaction of lactic acid performed in the lactic acid conversion tank.

Example 2

According to the process flow chart illustrated in FIG. 1, the acrylic acid producing process was simulated using Aspen Plus simulator available from Aspen Technology, Inc.

Specifically, a process was performed in the same manner as that of Example 1, except that 40 wt % of a lactic acid aqueous solution was supplied to a reactor, and the lower temperature of the first cooling tower 10 was controlled to 133° C.

In this case, the flow rate (kg/hr) and composition (wt %) of each component in each stream 1a through 12a of FIG. 1 are shown in Table 2.

TABLE 2

| Component | Unit | 1a | 2a | 3a | 4a | 5a | 6a | 7a | 8a | 9a | 10a | 11a | 12a |
|---|---|---|---|---|---|---|---|---|---|---|---|---|---|
| Flow rate | | 11000 | 3070 | 7930 | 1023 | 6907 | 24 | 2405 | 3145 | 1332 | 5475 | 5275 | 200 |
| $N_2$ | kg/hr | 1000 | 0 | 1000 | 1000 | 0 | 0 | 0 | 0 | 0 | 0 | 0 | 0 |
| Lactic acid | kg/hr | 2000 | 1565 | 202 | 0 | 202 | 1 | 81 | 0 | 120 | 1798 | 1782 | 17 |
| Water | kg/hr | 6420 | 934 | 5509 | 22 | 5487 | 23 | 2318 | 3145 | 0 | 3237 | 3237 | 0 |
| Acrylic acid | kg/hr | 1440 | 240 | 1200 | 1 | 1199 | 0 | 2 | 0 | 1197 | 241 | 241 | 0 |
| Heavy component | kg/hr | 140 | 122 | 19 | 0 | 19 | 0 | 4 | 0 | 15 | 126 | 15 | 111 |
| Lactic acid dimer | kg/hr | 0 | 209 | 0 | 0 | 0 | 0 | 0 | 0 | 0 | 73 | 0 | 73 |
| Composition | | | | | | | | | | | | | |
| $N_2$ | wt % | 9% | 0% | 13% | 98% | 0% | 0% | 0% | 0% | 0% | 0% | 0% | 0% |
| Lactic acid | wt % | 18% | 51% | 3% | 0% | 3% | 3% | 3% | 0% | 9% | 33% | 34% | 8% |
| Water | wt % | 58% | 30% | 69% | 2% | 79% | 96% | 96% | 100% | 0% | 59% | 61% | 0% |
| Acrylic acid | wt % | 13% | 8% | 15% | 0% | 17% | 0% | 0% | 0% | 90% | 4% | 5% | 0% |
| Heavy component | wt % | 1% | 4% | 0% | 0% | 0% | 0% | 0% | 0% | 1% | 2% | 0% | 55% |
| Lactic acid dimer | wt % | 0% | 7% | 0% | 0% | 0% | 0% | 0% | 0% | 0% | 1% | 0% | 36% |

As shown in Table 2 and FIG. 1, it could be confirmed that the recovery rate of lactic acid was 89.1% with reference to the mass flow rate (1,782 kg/hr) of lactic acid recovered through the stream No. 11a compared to the mass flow rate (2,000 kg/hr) of lactic acid introduced through the stream No. 1a. Furthermore, when the streams before and after being introduced into the lactic acid conversion tank 300 were compared with each other, it could be confirmed that lactic acid was increased by 15% by the reverse reaction of the oligomerization reaction of lactic acid performed in the lactic acid conversion tank.

COMPARATIVE EXAMPLES

Comparative Example 1

Figure 2:
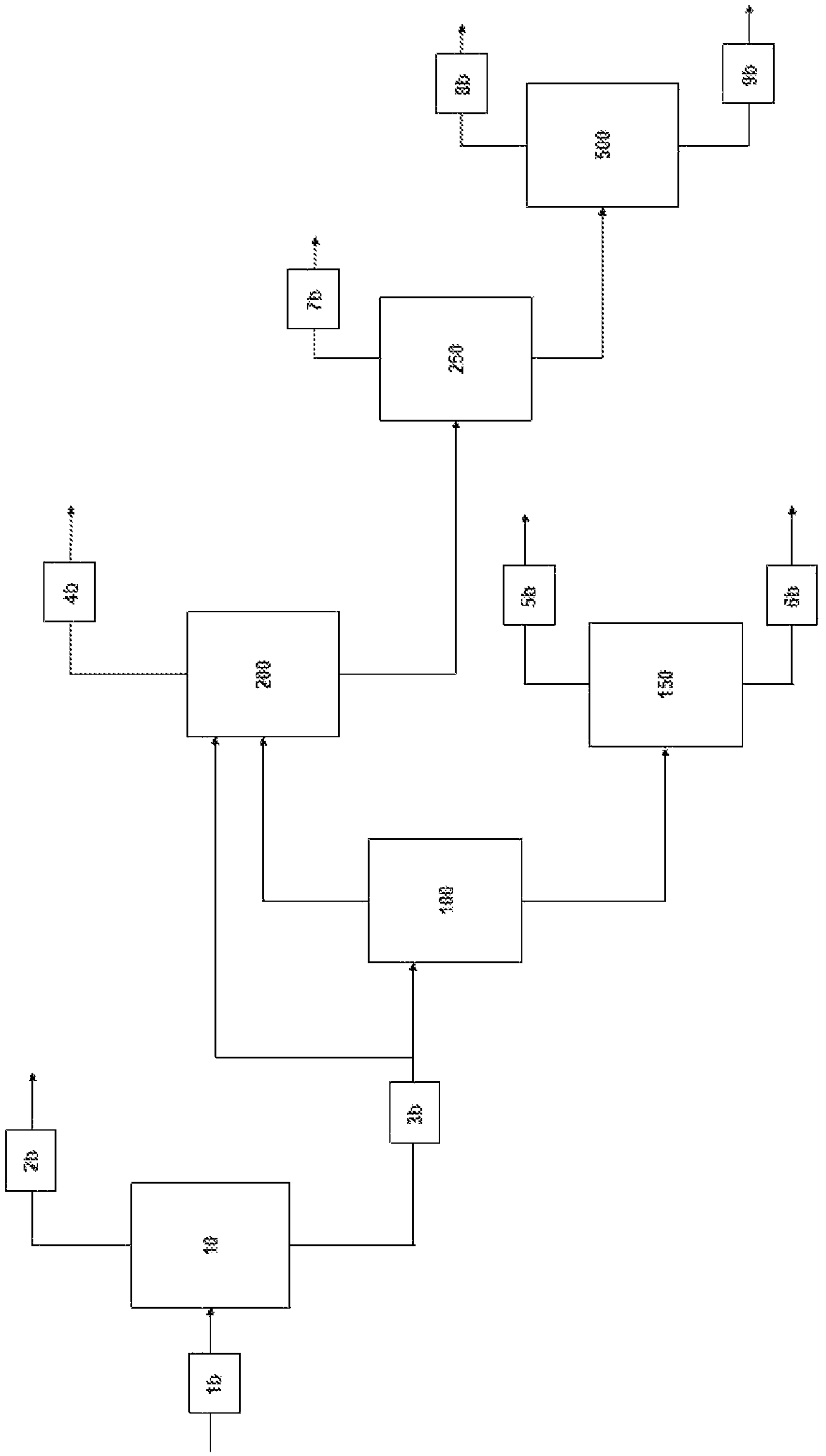
FIG. 2 is a process flow chart according to a method for preparing acrylic acid according to a comparative example for comparison with the present invention.

According to the process flow chart illustrated in FIG. 2, the acrylic acid producing process was simulated using Aspen Plus simulator available from Aspen Technology, Inc.

In Comparative Example 1, a light gas component was separated using one cooling tower, and an additional distillation column was used downstream of the extraction column and the azeotropic distillation column in order to implement the content of acrylic acid in the stream from which acrylic acid was recovered to 96 wt % as in Example 1.

As in Example 1, a reaction product was produced using a lactic acid aqueous solution in Comparative Example 1. Specifically, 30 wt % of a lactic acid aqueous solution and nitrogen ($N_2$) as a diluent gas were supplied to a reactor, and a reaction product including lactic acid, a lactic acid dimer, water, and acrylic acid was produced through a dehydration reaction.

The reaction product was supplied to the cooling tower 10, a light gas component such as nitrogen was separated through the upper discharge, and a stream containing lactic acid, a lactic acid dimer, acrylic acid, and water was separated through the lower discharge. At this time, a lower operating temperature and an upper operating pressure of the cooling tower 10 were controlled to 108° C. and 1.3 kg/cm$^2$, respectively.

Thereafter, a part of a lower discharge stream of the cooling tower 10 was supplied to the extraction column 100, a remainder was supplied to the azeotropic distillation column 200, and a ratio of a mass flow rate of the acrylic acid aqueous solution stream supplied to the extraction column 100 to a flow rate of the lower discharge stream of the cooling tower was maintained at 50 wt %.

Meanwhile, in the extraction column 100, acrylic acid was dissolved using toluene as an extraction solvent, and then an extract containing acrylic acid and an extraction solvent was separated through the upper discharge stream of the extraction column 100 and supplied to the azeotropic distillation column 200. Subsequently, distillation was performed in the azeotropic distillation column 200, and the upper discharge stream of the extraction column 100 was separated into a lower discharge stream containing lactic acid, a lactic acid dimer, and acrylic acid and an upper discharge stream containing water and an extraction solvent.

Lactic acid and a lactic acid dimer were contained in both the lower discharge stream of the extraction column and the lower discharge stream of the azeotropic distillation column, and first and second lactic acid separation columns 150 and 250 had to be introduced in order to separate lactic acid contained in each stream.

Specifically, lactic acid, a lactic acid dimer, and water contained in the lower discharge stream of the extraction column 100 were separated by the first lactic acid separation column 150 through distillation, and lactic acid, a lactic acid dimer, and acrylic acid contained in the lower discharge stream of the azeotropic distillation column 200 were separated by the second lactic acid separation column 250 through distillation.

Meanwhile, acrylic acid was obtained through the upper of the second lactic acid separation column 250, and the lower discharge stream of the second lactic acid separation column 250 was supplied to a heavy component separation column 500 and distilled, and therefore, lactic acid was separated through the upper of the heavy component separation column 500, and a lactic acid dimer and a heavy component were separated through the lower of the heavy component separation column 500.

The flow rate (kg/hr) and composition (wt %) of each component in each stream 1b through 9b in Comparative Example 1 (FIG. 2) are shown in Table 3.

TABLE 3

| Component | Unit | 1b | 2b | 3b | 4b | 5b | 6b | 7b | 8b | 9b |
|---|---|---|---|---|---|---|---|---|---|---|
| Flow rate | | 11000 | 1023 | 9977 | 4297 | 2684 | 811 | 1612 | 330 | 243 |
| $N_2$ | kg/hr | 1000 | 1000 | 0 | 0 | 0 | 0 | 0 | 0 | 0 |
| Lactic acid | kg/hr | 600 | 0 | 600 | 0 | 0 | 236 | 62 | 133 | 22 |
| Water | kg/hr | 7504 | 22 | 7482 | 4292 | 2670 | 521 | 0 | 14 | 0 |
| Acrylic acid | kg/hr | 1728 | 1 | 1727 | 5 | 14 | 3 | 1541 | 164 | 0 |
| Heavy component | kg/hr | 168 | 0 | 168 | 0 | 0 | 44 | 9 | 19 | 96 |
| Lactic acid dimer | kg/hr | 0 | 0 | 0 | 0 | 0 | 8 | 0 | 0 | 125 |
| Composition | | | | | | | | | | |
| $N_2$ | wt % | 9% | 98% | 0% | 0% | 0% | 0% | 0% | 0% | 0% |
| Lactic acid | wt % | 5% | 0% | 6% | 0% | 0% | 29% | 4% | 40% | 9% |
| Water | wt % | 68% | 2% | 75% | 100% | 99% | 64% | 0% | 4% | 0% |
| Acrylic acid | wt % | 16% | 0% | 17% | 0% | 1% | 0% | 96% | 50% | 0% |
| Heavy component | wt % | 2% | 0% | 2% | 0% | 0% | 5% | 1% | 6% | 39% |
| Lactic acid dimer | wt % | 0% | 0% | 0% | 0% | 0% | 1% | 0% | 0% | 52% |

As shown in Table 3 and FIG. 2, it could be confirmed that the recovery rate of lactic acid was 61.5% with reference to the mass flow rate (236+133 kg/hr) of lactic acid recovered through the stream Nos. 8b and 6b compared to the mass flow rate (600 kg/hr) of lactic acid introduced through the stream No. 1b.

Comparative Example 2

According to the process flow chart illustrated in FIG. 2, the acrylic acid producing process was simulated using Aspen Plus simulator available from Aspen Technology, Inc.

Specifically, a process was performed in the same manner as that of Comparative Example 1, except that 40 wt % of a lactic acid aqueous solution was supplied to a reactor, and the lower temperature of the cooling tower 10 was controlled to 109° C.

In Comparative Example 2, an additional distillation column was used downstream of the extraction column and the azeotropic distillation column in order to realize the content of acrylic acid in the stream from which acrylic acid was recovered to 90 wt % as in Example 2 compared to Example 2 in which 40 wt % of the lactic acid aqueous solution was supplied to the reactor.

The flow rate (kg/hr) and composition (wt %) of each component in each stream 1b through 9b in Comparative Example 2 (FIG. 2) are shown in Table 4.

TABLE 4

| Component | Unit | 1b | 2b | 3b | 4b | 5b | 6b | 7b | 8b | 9b |
|---|---|---|---|---|---|---|---|---|---|---|
| Flow rate | | 11000 | 1023 | 9977 | 3669 | 2092 | 1412 | 1332 | 880 | 592 |
| $N_2$ | kg/hr | 1000 | 1000 | 0 | 0 | 0 | 0 | 0 | 0 | 0 |
| Lactic acid | kg/hr | 2000 | 0 | 2000 | 0 | 0 | 695 | 131 | 549 | 37 |
| Water | kg/hr | 6420 | 22 | 6398 | 3669 | 2092 | 643 | 0 | 53 | 0 |
| Acrylic acid | kg/hr | 1440 | 1 | 1439 | 0 | 0 | 0 | 1197 | 242 | 0 |
| Heavy component | kg/hr | 140 | 0 | 140 | 0 | 0 | 20 | 4 | 36 | 80 |
| Lactic acid dimer | kg/hr | 0 | 0 | 0 | 0 | 0 | 55 | 0 | 0 | 475 |
| Composition | | | | | | | | | | |
| $N_2$ | wt % | 9% | 98% | 0% | 0% | 0% | 0% | 0% | 0% | 0% |
| Lactic acid | wt % | 18% | 0% | 20% | 0% | 0% | 49% | 10% | 62% | 6% |
| Water | wt % | 58% | 2% | 64% | 100% | 100% | 46% | 0% | 6% | 0% |
| Acrylic acid | wt % | 13% | 0% | 14% | 0% | 0% | 0% | 90% | 27% | 0% |

TABLE 4-continued

| Component | Unit | 1b | 2b | 3b | 4b | 5b | 6b | 7b | 8b | 9b |
|---|---|---|---|---|---|---|---|---|---|---|
| Heavy component | wt % | 1% | 0% | 1% | 0% | 0% | 1% | 0% | 4% | 14% |
| Lactic acid dimer | wt % | 0% | 0% | 0% | 0% | 0% | 4% | 0% | 0% | 80% |

As shown in Table 4 and FIG. 2, it could be confirmed that the recovery rate of lactic acid was 62.2% with reference to the mass flow rate (695+549 kg/hr) of lactic acid recovered through the stream Nos. 8b and 6b compared to the mass flow rate (2,000 kg/hr) of lactic acid introduced through the stream No. 1b.

The invention claimed is:

1. A method for preparing acrylic acid, the method comprising:

obtaining a first reaction product including lactic acid, a lactic acid dimer, water, and acrylic acid by supplying a lactic acid aqueous solution to a reactor to allow a dehydration reaction to proceed;

supplying the first reaction product to a first cooling tower to separate the first reaction product into a lower fraction of the first cooling tower containing lactic acid and a lactic acid dimer, and an upper fraction of the first cooling tower containing water and acrylic acid;

obtaining a second reaction product by supplying the lower fraction of the first cooling tower to a lactic acid conversion tank and converting the lactic acid dimer into lactic acid;

separating lactic acid from the second reaction product to recover lactic acid; and obtaining acrylic acid by separating acrylic acid from the upper fraction of the first cooling tower.

2. The method of claim 1, comprising supplying the second reaction product to a lactic acid purification column to recover lactic acid through the upper fraction of the lactic acid purification column.

3. The method of claim 1, wherein the lower fraction of the first cooling tower is supplied to the lactic acid conversion tank as a lower discharge stream of the first cooling tower, and a mass flow rate of lactic acid included in the second reaction product discharged from the lactic acid conversion tank is increased by 5 wt % to 20 wt % compared to a mass flow rate contained in the lower discharge stream of the first cooling tower.

4. The method of claim 1, wherein an operating temperature of the first cooling tower is 100° C. to 180° C. and an operating pressure of the first cooling tower is 1 $kg/cm^2$ to 20 $kg/cm^2$.

5. The method of claim 1, wherein the obtaining of the acrylic acid by separating the acrylic acid from the upper fraction of the first cooling tower includes:

supplying the upper fraction of the first cooling tower to an extraction column to separate the upper fraction of the first cooling tower into an extract containing acrylic acid and an extractant and a raffinate containing water;

obtaining acrylic acid by separating acrylic acid from the extract; and supplying the raffinate to the lactic acid conversion tank.

6. The method of claim 1, wherein the obtaining of the acrylic acid by separating the acrylic acid from the upper fraction of the first cooling tower includes:

supplying the upper fraction of the first cooling tower to a second cooling tower to separate a lower fraction of the second cooling tower containing acrylic acid and water;

supplying a part of the lower fraction of the second cooling tower to an extraction column as a first acrylic acid aqueous solution stream and supplying a remainder to an azeotropic distillation column as a second acrylic acid aqueous solution stream;

supplying a raffinate containing water obtained in the extraction column to the lactic acid conversion tank;

supplying an extract containing acrylic acid and an extraction solvent obtained in the extraction column to the azeotropic distillation column; and obtaining acrylic acid from a lower fraction of the azeotropic distillation column.

7. The method of claim 6, wherein an operating temperature of the second cooling tower is 60° C. to 140° C. and an operating pressure of the second cooling tower is 1 $kg/cm^2$ to 20 $kg/cm^2$.

8. The method of claim 6, wherein a ratio of a flow rate of the first acrylic acid aqueous solution stream supplied to the extraction column to the total flow rate of the first acrylic acid aqueous solution stream and the second acrylic acid aqueous solution stream is 30 wt % to 70 wt %.

9. The method of claim 6, wherein an upper fraction of the azeotropic distillation column is supplied to a layer separator to separate water and an extraction solvent, and circulating the separated extraction solvent is circulated to one or more of the extraction column and the azeotropic distillation column.

10. The method of claim 1, wherein in the lactic acid conversion tank, an oligomerization reaction of the lactic acid and a reverse reaction thereof are performed.

* * * * *